United States Patent
Harris et al.

(10) Patent No.: US 11,738,100 B2
(45) Date of Patent: Aug. 29, 2023

(54) FORMULATIONS AND KITS FOR RADIOTHERAPY AND DIAGNOSTIC IMAGING

(71) Applicant: Clarity Pharmaceuticals Limited, Eveleigh (AU)

(72) Inventors: Matthew John Harris, Hunters Hill (AU); Sean Lumb, Eveleigh (AU)

(73) Assignee: CLARITY PHARMACEUTICALS LIMITED, Eveleigh (AU)

(*) Notice: Subject to any disclaimer, the term of this patent is extended or adjusted under 35 U.S.C. 154(b) by 0 days.

(21) Appl. No.: 17/042,772

(22) PCT Filed: Apr. 11, 2019

(86) PCT No.: PCT/AU2019/050324
§ 371 (c)(1),
(2) Date: Sep. 28, 2020

(87) PCT Pub. No.: WO2019/195890
PCT Pub. Date: Oct. 17, 2019

(65) Prior Publication Data
US 2021/0015950 A1    Jan. 21, 2021

(30) Foreign Application Priority Data

Apr. 11, 2018  (AU) ................... 2018901195
Apr. 11, 2018  (AU) ................... 2018901196

(51) Int. Cl.
| | | |
|---|---|---|
| A61K 51/00 | (2006.01) |
| A61M 36/14 | (2006.01) |
| A61K 51/04 | (2006.01) |
| A61K 9/08 | (2006.01) |
| A61K 49/10 | (2006.01) |
| A61P 35/00 | (2006.01) |
| A61K 31/495 | (2006.01) |
| A61K 31/395 | (2006.01) |

(52) U.S. Cl.
CPC ............ *A61K 51/0482* (2013.01); *A61K 9/08* (2013.01); *A61K 49/106* (2013.01); *A61K 31/395* (2013.01); *A61K 31/495* (2013.01); *A61K 51/044* (2013.01); *A61K 51/0497* (2013.01); *A61P 35/00* (2018.01)

(58) Field of Classification Search
CPC .... A61K 51/0482; A61K 9/08; A61K 49/106; A61K 51/044; A61K 51/0497; A61K 31/395; A61K 51/0495; A61K 31/495; A61P 35/00
See application file for complete search history.

(56) References Cited

U.S. PATENT DOCUMENTS

| | | |
|---|---|---|
| 9,701,694 B2 * | 7/2017 | Donnelly ............ A61K 51/0482 |
| 2005/0180918 A1 | 8/2005 | Cyr et al. |
| 2007/0269375 A1 * | 11/2007 | Chen ...................... A61P 35/00 |
| | | 424/1.69 |
| 2016/0331852 A1 | 11/2016 | Zeglis et al. |

FOREIGN PATENT DOCUMENTS

| | | |
|---|---|---|
| WO | 03-092743 A1 | 11/2003 |
| WO | 2011-147762 A2 | 12/2011 |
| WO | 2013-029616 A1 | 3/2013 |
| WO | 2013-082656 A1 | 6/2013 |
| WO | 2018-081860 A1 | 5/2018 |
| WO | 2018-223180 A1 | 12/2018 |

OTHER PUBLICATIONS

Alt et al. (Angew. Chem. Int. Ed. 2015, 54, 7515-7519).*
Paterson et al. (Dalton Trans. 2014, 43, 1386-1396).*
International Search Report and Written Opinion mailed in International Patent Application No. PCT/AU2019/050324, filed Apr. 11, 2019, 15 pages.
Zeglis, B., et al., "Optimization of a Pretargeted Strategy for the PET Imaging of Colorectal Carcinoma via the Modulation of Radioligand Pharmacokinetics." Molecular pharmaceutics, vol. 12, Issue 10, (Year 2015): 3575-87, DOI:10.1021/acs.molpharmaceut.5b00294.
Chen, J., et al., "Evaluation of radiostabilizers for formulated 177Lu-AMBA, a systemic radiotherapeutic agent for GRP receptor positive tumors", The Journal of Nuclear Medicine, vol. 47, No. suppl. 1, (year 2006), 161 p, 2 pages.

* cited by examiner

*Primary Examiner* — Michael G. Hartley
*Assistant Examiner* — Melissa J Perreira
(74) *Attorney, Agent, or Firm* — Kilpatrick Townsend & Stockton

(57) ABSTRACT

Aqueous formulations and kits of radiopharmaceutical compounds of general Formula (II) protected from radiolysis with stabilisers, such as L-methionine and gentisic acid, are disclosed, wherein the compounds are based on sarcophagine ligands coordinated to a radioisotope, such as 64-copper, and linked to a tetrazine group for reaction with tumour targeting antibodies having functional reactive groups such as trans-cyclooctene, processes of preparing said radioligand formulations, and uses thereof for radioimaging, diagnosing and treating cancer.

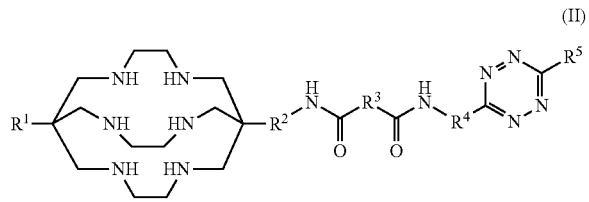

12 Claims, No Drawings

FORMULATIONS AND KITS FOR RADIOTHERAPY AND DIAGNOSTIC IMAGING

FIELD

The present invention relates to formulations and kits of compounds that are of use in radiotherapy and diagnostic imaging.

BACKGROUND

Macrocyclic ligands may be used as radiopharmaceuticals in applications such as radiotherapy or as diagnostic ligands for tumours or cancers. Of particular use, are radiolabeled ligands that show some propensity for selectively targeting a particular site in vivo (for example, a particular receptor), can retain a radioisotope, and subsequently deliver the radioisotope to the desired site of action. This requires that the ligand comprises a component to complex the radioisotope and a further component to target the desired site. Traditionally, ligands directly target a particular site, for example, a particular receptor that is characteristic for a tumour or cancer site. This direct targeting relies on an interaction between the ligand and receptor that is specific to the particular ligand and receptor and that the binding is sufficiently strong. Where the ligand does not bind strongly, the ligand (and accompanying radioisotope) can circulate, such that the radioisotope causes unwanted damage to other sites.

A known problem associated with macrocyclic ligands is that they may be complex organic compounds with various functional groups and subsequently, reactive centres. This may mean that the ligand itself may decompose under particular conditions and be rendered useless. Another problem associated with the ligand itself is that it may have limited solubility in particular solvents. Aside from solubility issues, the ligand may also be unstable and decompose in particular solvents. Ideally, the ligand is sufficiently soluble and stable in a pharmaceutically acceptable solvent, where the ligand is to be administered for therapeutic purposes. Even if a ligand is sufficiently stable and soluble in a given solvent, the ligand complexed with a metal ion may have different properties and thus display a different stability and solubility profile.

Where the macrocyclic ligand is complexed with a metal ion that is a radioisotope, this may result in radiolysis. This results from the spontaneous radioactive decay of the radioisotope and subsequent release of radiation, such that the energy released may be sufficient to induce cleavage of bonds and cause destruction of the ligand. In addition to reducing the overall efficacy of the complexed ligand, the release of the radioisotope also results in the delivery of radiation to unwanted sites.

As many radiopharmaceuticals are designed to be administered parenterally, i.e. as an injectable and usually as a solution, the ligand itself must be soluble in a pharmaceutically acceptable solvent or carrier. As is known in the art, the solubility of a particular compound in any given solvent may be unpredictable. Although the solubility of a particular compound in a particular solvent may be known, the solubility of an analogue of the compound in a different solvent system may be quite different. This then presents added difficulties to one seeking to develop a formulation of a compound and especially a pharmaceutically acceptable injectable formulation.

Pharmaceutical formulations typically include one or more excipients that affect the compound in some way, such as the enhancement of solubility of the compound or increasing stability of the compound while in solution. Alternatively, additional excipients may be used to provide other features to the formulation, such as preservatives, buffers and the like.

While many thousands of formulations of ligand-radioisotope complexes have been documented, there is no expectation that the excipients used in such formulations would provide the required solubility and bioavailability of any newly developed complex. Furthermore, one cannot expect that a particular combination of excipients would further prevent or minimise the dissociation of the radioisotope or minimise radiolysis from occurring.

Accordingly, desirable formulations of ligand-radioisotope complexes need to be tailored in order to display the requisite stability in relation to radiolysis and dissociation of the radioisotope, while also being pharmaceutically acceptable. The present invention seeks to address these problems in relation to a specific ligand complex.

The time for which the ligand-radioisotope complex is effective is ideally maximized. This would require that the formulation comprising the ligand-radioisotope complex is prepared just prior to administration to the patient. While this may be possible for patients situated in close proximity to a synchrotron or other source of the radioisotope, this will not be the case for many other patients. These patients may require that the formation be transported across vast distances, which reduces the time for which the ligand-radioisotope complex is effective. Accordingly, there exists a need for ways to provide the ligand-radioisotope complex to facilities located a considerable distance away from the source of the radioisotope.

SUMMARY OF THE INVENTION

The present invention relates to formulations and kits of compounds that are may be used as ligands, however the ligands do not necessarily target the intended tumour or cancer site. The compounds of the formulations and kits disclosed herein do not bind directly to a tumour or cancer site, but instead targets an intermediate compound that binds to a tumour or cancer site. The compounds of the kits and formulations contain a functional group that can react selectively with the intermediate compound. Advantages of this approach are that the compounds of the formulations and kits can then bind more selectively and securely to the intermediate compound (as compared to the direct binding to a tumour or cancer site), such that the efficacy of the administered formulation is greater due and less is lost due to diffusion or weak binding to the target site. This then means that the dose administered through the formulation can be optimized, such that a smaller dose is administered, without any loss in overall efficacy. This also leads to smaller amounts of the compound and radioisotope being administered or lost.

According to a first aspect of the present invention, there is provided an aqueous formulation comprising a compound of Formula (I), or a salt thereof,

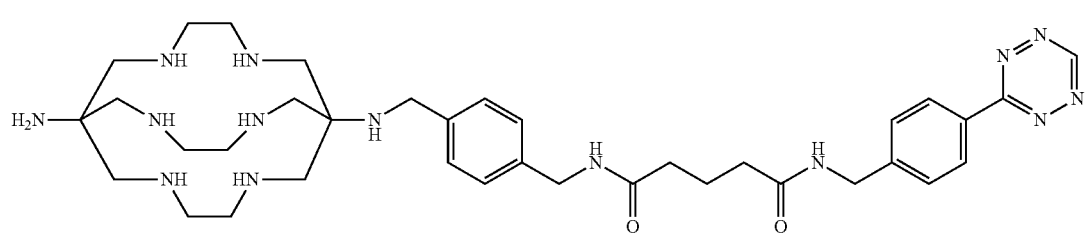

Formula (I)

the formulation further comprising sodium chloride and one or more stabilizers selected from the group consisting of thiosulfates, ascorbates, ascorbic acid, gentisates, gentisic acid, methionine, maltose, inositol, benzyl alcohol, trehalose, povidone, niacinamide, cysteine and salts thereof.

In an embodiment of the first aspect, the aqueous formulation includes ethanol.

In another embodiment of the first aspect, the aqueous formulation includes L-methionine, or a salt thereof, as a stabiliser.

According to a second aspect of the present invention, there is provided an aqueous formulation comprising a compound of Formula (I), or a salt thereof,

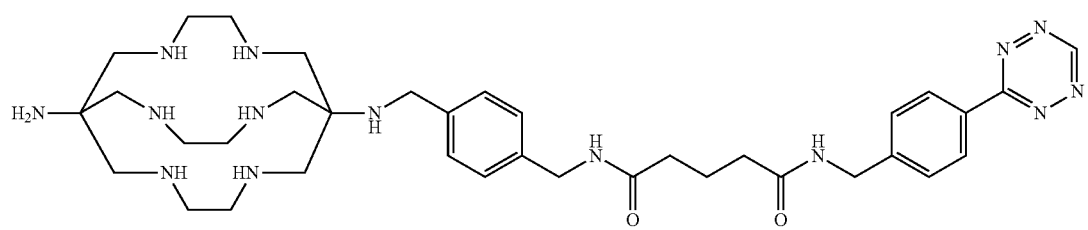

Formula (I)

the formulation further comprising:
  sodium chloride;
  one or more stabilizers selected from the group consisting of thiosulfates, ascorbates, ascorbic acid, gentisates, gentisic acid, methionine, maltose, inositol, benzyl alcohol, trehalose, povidone, niacinamide, cysteine and salts thereof;
  ethanol; and
  wherein a stabilizer is L-methionine, or a salt thereof.

In an embodiment of the second aspect, the aqueous formulation includes an acetate salt.

According to a third aspect of the present invention, there is provided an aqueous formulation comprising a compound of Formula (I), or a salt thereof, the formulation further comprising:
  sodium chloride;
  one or more stabilizers selected from the group consisting of thiosulfates, ascorbates, ascorbic acid, gentisates, gentisic acid, methionine, maltose, inositol, benzyl alcohol, trehalose, povidone, niacinamide, cysteine and salts thereof;
  ethanol; and
  an acetate salt;
  wherein a stabilizer is L-methionine, or a salt thereof.

According to a fourth aspect of the present invention, there is provided a process for preparing an aqueous formulation comprising a compound of Formula (I), or a salt thereof, complexed with a Cu ion, the process comprising the steps of:
  i) preparing a buffer solution of an acetate salt, wherein the buffering solution further comprises ethanol and one or more stabilizers selected from the group consisting of thiosulfates, ascorbates, ascorbic acid, gentisates, gentisic acid, methionine, maltose, inositol, benzyl alcohol, trehalose, povidone, niacinamide, cysteine and salts thereof;
  ii) dissolving a compound of Formula (I), or a salt thereof, in the buffering solution obtained from step i);
  iii) adding a solution of a Cu ion to the solution obtained from step ii);
  iv) filtering the solution obtained from step iii) on to a stationary phase; and

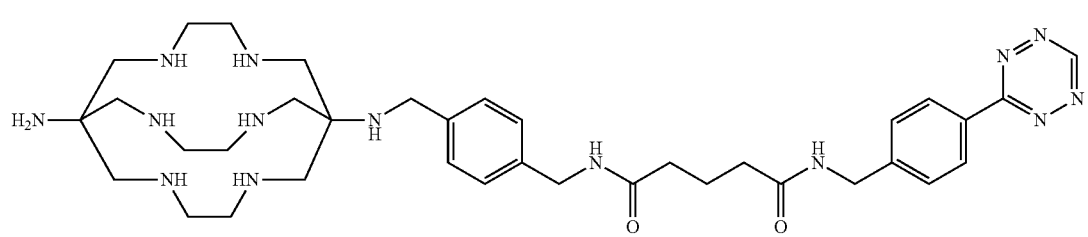

Formula (I)

v) washing the stationary phase of step iv) with ethanol and saline into a solution of L-methionine;

to recover an aqueous formulation comprising a compound of Formula (I), or a salt thereof, complexed with a Cu ion.

According to a fifth aspect of the present invention, there is provided an aqueous formulation prepared by a process as defined in an earlier aspect.

According to a sixth aspect of the present invention, there is provided a kit comprising a compound of Formula (II), or a pharmaceutically acceptable salt thereof, complexed with a Cu ion:

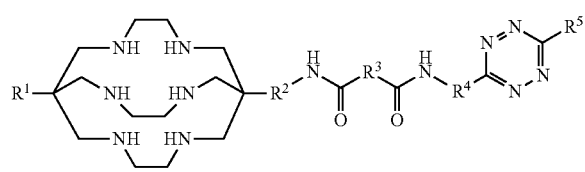

the kit comprising:
- a container comprising a compound of Formula (II), or a pharmaceutically acceptable salt thereof;
- a container comprising a solution of a Cu ion; and
- instructions for preparing an aqueous formulation of a compound of Formula (II), or a salt thereof, complexed with a Cu ion, including the addition of a solution of ethanol and one or more stabilisers selected from the group consisting of thiosulfates, ascorbates, ascorbic acid, gentisates, gentisic acid, methionine, maltose, inositol, benzyl alcohol, trehalose, povidone, niacinamide, cysteine and salts thereof, wherein:

$R^1$ is H, optionally substituted alkyl or optionally substituted amino;

$R^2$, $R^3$ and $R^4$ are linker groups; and $R^5$ is H, optionally substituted alkyl, optionally substituted aryl or optionally substituted heteroaryl.

In an embodiment of the sixth aspect, the kit further comprises a container of a compound that can bind to a tumour or cancer site and comprises a functional group that reacts with a tetrazine moiety of the compound of Formula (II).

According to an seventh aspect of the present invention, there is provided an aqueous formulation of a compound of Formula (II), or a salt thereof, complexed with a Cu ion, prepared according to a kit as defined in the seventh aspect.

According to an eighth aspect of the present invention, there is provided a method for radioimaging, diagnosing or treating a cancer, the method comprising administering to a subject in need thereof an aqueous formulation according to any one of the first to third, fifth or seventh aspects.

DETAILED DESCRIPTION

The present invention relates to stable formulations of a macrocyclic ligand and metal complexes thereof. The present inventors have found that the formulations of the macrocyclic ligand as disclosed herein are stable with respect to the free ligand. The present inventors have also found that the formulations of a metal complex of the macrocyclic ligand as disclosed herein minimise dissociation of the complexed metal from the ligand and also minimise radiolysis of the ligand where the metal is a radioisotope.

The formulations of the macrocyclic ligand and metal complexes thereof are stable in solution and under physiological conditions for a time. Where the formulation comprises a metal complex of the macrocyclic ligand, the stability of the formulation relates to the stability of the complex, where the metal is a radioisotope that may undergo dissociation or where the complex may under radiolysis. The stability of a formulation comprising a radioisotope-ligand complex can be measured by considering the radiochemical purity of the formulation. Radiochemical purity is defined as the amount of the radioisotope complexed by the sarcophagine ligand expressed as percentage of the total amount of the radioisotope present in the formulation. The radioisotope may be present in the formulation as a complex with the sarcophagine ligand, as a free radioisotope or as part of a radiolysis product.

It has been found that the tetrazine-substituted ligands, such as those of Formula (I), can target a transcyclooctene moiety and undergo and the tetrazine and transcyclooctene functional groups undergo an inverse electron demand Diels-Alder reaction to produce the corresponding click chemistry conjugate. Where the transcyclooctene functionality is installed on a target in vivo in a pretargeting strategy, this allows for a tetrazine-substituted ligand complexed with a radioactive isotope to bind selectively to the transcyclooctene site and subsequently deliver the radioisotope to the desired site of action. The radioactivity derived from radioisotope is often used to for radiotherapy in the treatment of tumours. This pretargeting strategy requires that the antibodies that bind to the surface of the tumour be modified to include the transcyclooctene moiety, followed by the administration of the modified antibodies to allow them to bind to the tumour sites. This is then followed by the administration of the tetrazine-substituted ligand bearing a radioisotope, which selectively binds to the modified antibodies, thus delivering the radioisotope to the desired site of action.

An example of a tetrazine-substituted ligand includes the compound of Formula (I):

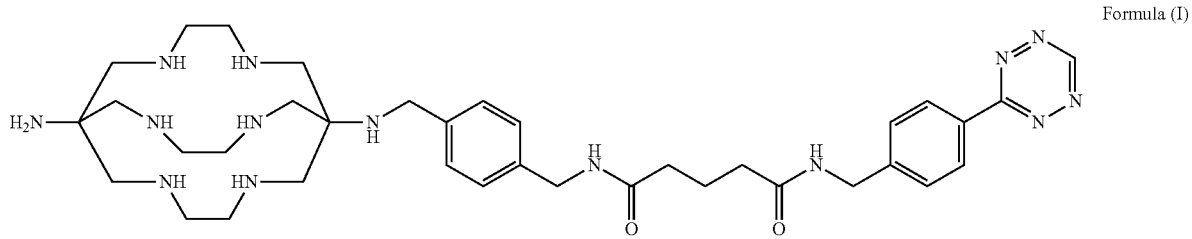

Formula (I)

The compound of Formula (I) is a macrocyclic sarcophagine ligand, where the tetrazine moiety is bound to the sarcophagine through a series of linking groups. The sarcophagine, or 3,6,10,13,16,19-hexaazabicyclo[6.6.6]eicosane, has an amino group at one terminal position, with successive aminobenzyl, propyl and benzyl groups linked by amide bonds. A person skilled in the art would understand that a sarcophagine (or "sar") is a nitrogen-containing hexadentate macrocyclic ligand, which is capable of complexing donor atoms, such as transition metal ions and in the context of the present invention, Cu ions and radioisotopes thereof.

The compound of Formula (I) may be produced via a series of coupling reactions between a diaminosarcophagine and suitable coupling partners. The synthetic route to access the compound of Formula (I) has been previously disclosed in *Mol. Pharm.*, 2015, 12, 10, 3375.

The present invention also contemplates the use of pharmaceutically acceptable salts of the compound of Formula (I), as part of the claimed formulations. Examples of pharmaceutically acceptable salts of compounds of Formula (I) may include the corresponding acetate salt, sodium salt, hydrochloride salt, potassium salt, magnesium salt, calcium salt or ammonium salt. In an embodiment, the compound of Formula (I) is provided as the acetate salt.

The administrable formulations of the present invention comprise a complex of a compound of Formula (I), or a salt thereof, and a radioisotope. The radioisotope, may also be referred to as a radionuclide, and may be a metal or a metal ion. The ligand of the present specification has been found to be particularly successful in complexing copper ions, especially $Cu^{2+}$ ions. The complex of the Formula (I), comprising a copper ion radioisotope has been previously disclosed in *Mol. Pharm.*, 2015, 12, 10, 3375. A person skilled in the art would also appreciate that a complex of Formula (I) and a radioisotope may be achieved by contacting the compound of Formula (I), or a salt thereof, with the radioisotope that is to be complexed, such that the compound of Formula (I), or a salt thereof, is complexed with the radioisotope. This may involve the mixing of the compound of Formula (I), or a salt thereof, and the radioisotope in a suitable solvent system (such as that specifically described herein).

In an embodiment, the ligand is complexed with a Cu ion. The copper ion may be radioactive, and thus a radionuclide or radioisotope of copper. In an embodiment, the ligand is complexed with $^{60}Cu$. In another embodiment, the ligand is complexed with $^{61}Cu$. In another embodiment, the ligand is complexed with $^{64}Cu$. In another embodiment, the ligand is complexed with $^{67}Cu$. In a preferred embodiment, the ligand is complexed with $^{64}Cu$. In another preferred embodiment, the ligand is complexed with $^{67}Cu$.

According to an aspect of the present invention, there is provided an aqueous formulation comprising a compound of Formula (I), or a salt thereof, the formulation further comprising sodium chloride and a stabilizer, or a salt thereof.

In an embodiment, sodium chloride is present in the formulation in an amount of about 0.6% to 1.2% (w/v). In an embodiment, sodium chloride is present in an amount of about 0.6% (w/v). In another embodiment, sodium chloride is present in an amount of about 0.7% (w/v). In another embodiment, sodium chloride is present in an amount of about 0.8% (w/v). In another embodiment, sodium chloride is present in an amount of about 0.9% (w/v). In another embodiment, sodium chloride is present in an amount of about 1.0% (w/v). In another embodiment, sodium chloride is present in an amount of about 1.1% (w/v). In another embodiment, sodium chloride is present in an amount of about 1.2% (w/v). In a preferred embodiment, sodium chloride is present in the formulation in an amount of about 0.9% (w/v). In other embodiments, the present invention also contemplates sodium chloride in ranges between the aforementioned amounts.

The formulations of the present invention comprise one or more stabilizers as a component. It has been identified by the present inventors that the presence of a stabilizer in the present formulations assists in preventing or minimising radiolysis of the radiolabelled complex of Formula (I). Examples of stabilizers that may be used in the present formulations include thiosulfates, ascorbates, ascorbic acid, gentisates, gentisic acid, methionine, maltose, inositol, benzyl alcohol, trehalose, povidone, niacinamide, cysteine and where appropriate, salts thereof.

In an embodiment, a formulation of the present invention comprises one or more stabilizers in a total amount of about 0.02% to about 0.1% (w/v). In an embodiment, a formulation of the present invention comprises one or more stabilizers in a total amount of about 0.02% (w/v). In another embodiment, a formulation of the present invention comprises one or more stabilizers in a total amount of about 0.025% (w/v). In another embodiment, a formulation of the present invention comprises one or more stabilizers in a total amount of about 0.03% (w/v). In another embodiment, a formulation of the present invention comprises one or more stabilizers in a total amount of about 0.035% (w/v). In another embodiment, a formulation of the present invention comprises one or more stabilizers in a total amount of about 0.04% (w/v). In another embodiment, a formulation of the present invention comprises one or more stabilizers in a total amount of about 0.045% (w/v). In another embodiment, a formulation of the present invention comprises one or more stabilizers in a total amount of about 0.05% (w/v). In another embodiment, a formulation of the present invention comprises one or more stabilizers in a total amount of about 0.055% (w/v). In another embodiment, a formulation of the present invention comprises one or more stabilizers in a total amount of about 0.6% (w/v). In another embodiment, a formulation of the present invention comprises one or more

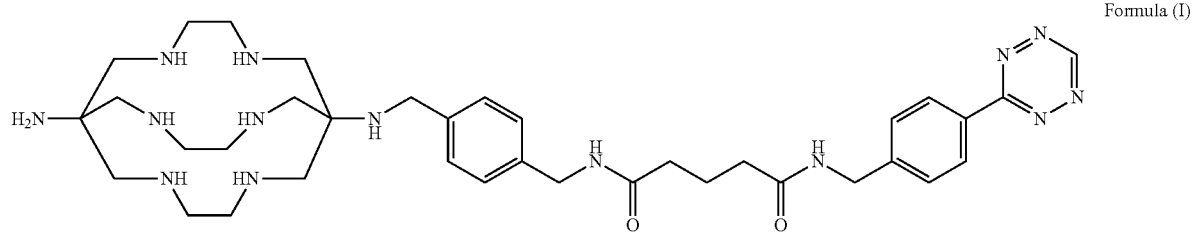

Formula (I)

stabilizers in a total amount of about 0.065% (w/v). In another embodiment, a formulation of the present invention comprises one or more stabilizers in a total amount of about 0.07% (w/v). In another embodiment, a formulation of the present invention comprises one or more stabilizers in a total amount of about 0.075% (w/v). In another embodiment, a formulation of the present invention comprises one or more stabilizers in a total amount of about 0.08% (w/v). In another embodiment, a formulation of the present invention comprises one or more stabilizers in a total amount of about 0.085% (w/v). In another embodiment, a formulation of the present invention comprises one or more stabilizers in a total amount of about 0.09% (w/v). In another embodiment, a formulation of the present invention comprises one or more stabilizers in a total amount of about 0.095% (w/v). In another embodiment, a formulation of the present invention comprises one or more stabilizers in a total amount of about 0.1% (w/v). In other embodiments, the present invention also contemplates one or more stabilizers present in ranges between the aforementioned amounts.

In an embodiment, the formulation comprising a compound of Formula (I) comprises L-methionine, or a salt thereof, as a stabiliser. The term L-methionine as used herein refers to the amino acid bearing an S-methyl thioether side chain. The addition of L-methionine to a formulation of the present invention further enhances the stability of the formulation by preventing or minimising radiolysis of a radiolabelled complex of Formula (I), thereby increasing the radiochemical purity of the formulation. The present inventors have found that the addition of L-methionine to a formulation comprising a compound of Formula (I) and a Cu ion allows for a formulation with a higher starting radioactivity to be obtained, where the Cu ion is a radioisotope of Cu. This means that the dose of radioactivity that is delivered by the formulation comprising a compound of Formula (I) and the complexed Cu radioisotope may be higher than the same formulation without the addition of L-methionine.

In an embodiment, L-methionine, or a salt thereof, is present in the formulation in an amount of about 1 mg/mL to about 4 mg/mL. In an embodiment, L-methionine, or a salt thereof, is present in the formulation in an amount of about 1.0 mg/mL. In another embodiment, L-methionine, or a salt thereof, is present in the formulation in an amount of about 1.5 mg/mL. In another embodiment, L-methionine, or a salt thereof, is present in the formulation in an amount of about 2.0 mg/mL. In another embodiment, L-methionine, or a salt thereof, is present in the formulation in an amount of about 2.5 mg/mL. In another embodiment, L-methionine, or a salt thereof, is present in the formulation in an amount of about 3.0 mg/mL. In another embodiment, L-methionine, or a salt thereof, is present in the formulation in an amount of about 3.5 mg/mL. In another embodiment, L-methionine, or a salt thereof, is present in the formulation in an amount of about 4.0 mg/mL.

In another embodiment, gentisic acid, or a salt thereof, is present as a stabilizer in the formulation. Gentisic acid is also known as 2,5-dihydroxybenzoic acid, 5-hydroxysalicylic acid or hydroquinonecarboxylic acid. Salts of gentisic acid may include the sodium salt and the sodium salt hydrate. Any reference to gentisic acid may include a reference to salts thereof, where relevant.

In another embodiment, ascorbic acid, or a salt thereof, is present as a stabilizer in the formulation. Ascorbic acid is also known as L-ascorbic acid or Vitamin C. Salts of ascorbic acid include sodium ascorbate, calcium ascorbate, potassium ascorbate and sodium ascorbyl phosphate. Derivatives of ascorbic acid are also contemplated. These include fatty acid esters of ascorbic acid, such as the palmitate ester of ascorbic acid, i.e. ascorbyl palmitate.

According to another aspect of the present invention, there is provided an aqueous formulation comprising a compound of Formula (I), or a salt thereof, the formulation further comprising:
  sodium chloride;
  one or more stabilizers selected from the group consisting of thiosulfates, ascorbates, ascorbic acid, gentisates, gentisic acid, methionine, maltose, inositol, benzyl alcohol, trehalose, povidone, niacinamide, cysteine and salts thereof;
  ethanol; and
  wherein a stabilizer is L-methionine, or a salt thereof.

In another embodiment of the present invention, the aqueous formulation includes an acetate salt. The acetate salt of the aqueous formulation may be an acetate salt, which acts as a buffering salt. The acetate salt may be ammonium acetate or sodium acetate. The acetate salt may be provided as part of a buffering solution that is used as part of the formulation.

Accordingly, in yet another aspect of the present invention, there is provided an aqueous formulation comprising a compound of Formula (I), or a salt thereof, the formulation further comprising:
  sodium chloride;
  one or more stabilizers selected from the group consisting of thiosulfates, ascorbates, ascorbic acid, gentisates, gentisic acid, methionine, maltose, inositol, benzyl alcohol, trehalose, povidone, niacinamide, cysteine and salts thereof;
  ethanol;
  wherein a stabilizer is L-methionine, or a salt thereof; and
  an acetate salt.

The formulations of the present invention have a pH of about 4 to about 8. A person skilled in the art would understand that the pH of the formulation is an inherent characteristic of the formulation, attributed to the combination of the compound of Formula (I) or a complex thereof, and the remaining excipients of the formulation. The present inventors have found that this pH range provides for optimal radiolabelling efficiency, and also stability of the radiolabelled complex both in the formulation and when administered in vivo.

In an embodiment, the pH of the formulation is from about 4 to about 8. In an embodiment, the pH of the formulation is about 4. In another embodiment, the pH of the formulation is about 4.5. In another embodiment, the pH of the formulation is about 5.0. In an embodiment, the pH of the formulation is about 5.5. In another embodiment, the pH of the formulation is about 5.6. In another embodiment, the pH of the formulation is about 5.7. In another embodiment, the pH of the formulation is about 5.8. In another embodiment, the pH of the formulation is about 5.9. In another embodiment, the pH of the formulation is about 6.0. In another embodiment, the pH of the formulation is about 6.1. In another embodiment, the pH of the formulation is about 6.2. In another embodiment, the pH of the formulation is about 6.3. In another embodiment, the pH of the formulation is about 6.4. In another embodiment, the pH of the formulation is about 6.5. In another embodiment, the pH of the formulation is about 7.0. In another embodiment, the pH of the formulation is about 7.5. In another embodiment, the pH of the formulation is about 8.0. In a preferred embodiment, the pH of the formulation is about 6.0.

In a further embodiment, the aqueous formulation of the present invention comprises a compound of Formula (I), or a salt thereof, complexed with a Cu ion, about 10% (v/v) ethanol, about 0.9% (w/v) sodium chloride, about 0.06% gentisic acid, or a salt thereof, and about 2.5 mg/mL L-methionine, or a salt thereof, wherein the formulation has a pH of about 6.0. In another embodiment, the aqueous formulation of the present invention comprises a compound of Formula (I), or a salt thereof, complexed with a Cu ion, about 10% (v/v) ethanol, about 0.9% (w/v) sodium chloride, not more than 0.056% gentisic acid, or a salt thereof, and about 2.5 mg/mL L-methionine, or a salt thereof, wherein the formulation has a pH of about 6.0. In a further embodiment, the aqueous formulation of the present invention comprises a compound of Formula (I), or a salt thereof, complexed with a Cu ion, about 10% (v/v) ethanol, about 0.9% (w/v) sodium chloride, 0.056% gentisic acid, or a salt thereof, and about 2.5 mg/mL L-methionine, or a salt thereof, wherein the formulation has a pH of about 6.0. One skilled in the art would appreciate that the amount of the Formula (I)-Cu ion complex present in the aqueous formulation can be modified to suit varying needs.

In a further embodiment, the aqueous formulation of the present invention comprises a compound of Formula (I), or a salt thereof, complexed with a $^{64}$Cu ion, about 10% (v/v) ethanol, about 0.9% (w/v) sodium chloride, about 0.06% gentisic acid, or a salt thereof, and about 2.5 mg/mL L-methionine, or a salt thereof, wherein the formulation has a pH of about 6.0. In an embodiment, the aqueous formulation of the present invention comprises a compound of Formula (I), or a salt thereof, complexed with a $^{64}$Cu ion, about 10% (v/v) ethanol, not more than 0.9% (w/v) sodium chloride, not more than 0.056% gentisic acid, or a salt thereof, and about 2.5 mg/mL L-methionine, or a salt thereof, wherein the formulation has a pH of about 6.0. In a further embodiment, the aqueous formulation of the present invention comprises a compound of Formula (I), or a salt thereof, complexed with a $^{64}$Cu ion, about 10% (v/v) ethanol, about 0.9% (w/v) sodium chloride, about 0.056% gentisic acid, or a salt thereof, and about 2.5 mg/mL L-methionine, or a salt thereof, wherein the formulation has a pH of about 6.0.

In a further embodiment, the aqueous formulation of the present invention comprises a compound of Formula (I), or a salt thereof, complexed with a $^{67}$Cu ion, about 10% (v/v) ethanol, about 0.9% (w/v) sodium chloride, about 0.06% gentisic acid, or a salt thereof, and about 2.5 mg/mL L-methionine, or a salt thereof, wherein the formulation has a pH of about 6.0. In an embodiment, the aqueous formulation of the present invention comprises a compound of Formula (I), or a salt thereof, complexed with a $^{67}$Cu ion, about 10% (v/v) ethanol, not more than 0.9% (w/v) sodium chloride, not more than 0.056% gentisic acid, or a salt thereof, and about 2.5 mg/mL L-methionine, or a salt thereof, wherein the formulation has a pH of about 6.0. In a further embodiment, the aqueous formulation of the present invention comprises a compound of Formula (I), or a salt thereof, complexed with a $^{67}$Cu ion, about 10% (v/v) ethanol, about 0.9% (w/v) sodium chloride, about 0.056% gentisic acid, or a salt thereof, and about 2.5 mg/mL L-methionine, or a salt thereof, wherein the formulation has a pH of about 6.0.

In a further embodiment, the aqueous formulation of the present invention comprises a compound of Formula (I) as the acetate salt, complexed with a $^{64}$Cu ion, about 10% (v/v) ethanol, about 0.9% (w/v) sodium chloride, about 0.06% gentisic acid, or a salt thereof, and about 2.5 mg/mL L-methionine, or a salt thereof, wherein the formulation has a pH of about 6.0. In another embodiment, the aqueous formulation of the present invention comprises a compound of Formula (I) as the acetate salt, complexed with a $^{64}$Cu ion, about 10% (v/v) ethanol, about 0.9% (w/v) sodium chloride, about 0.056% gentisic acid, or a salt thereof, and about 2.5 mg/mL L-methionine, or a salt thereof, wherein the formulation has a pH of about 6.0. In another embodiment, the aqueous formulation of the present invention comprises a compound of Formula (I) as the acetate, salt, complexed with a $^{64}$Cu ion, about 10% ethanol, about 0.9% (w/v) sodium chloride, not more than 0.056% gentisic acid, or a salt thereof, and about 2.5 mg/mL L-methionine, or a salt thereof, wherein the formulation has a pH of about 6.0.

In a further embodiment, the aqueous formulation of the present invention comprises a compound of Formula (I) as the acetate salt, complexed with a $^{67}$Cu ion, about 10% (v/v) ethanol, about 0.9% (w/v) sodium chloride, about 0.06% gentisic acid, or a salt thereof, and about 2.5 mg/mL L-methionine, or a salt thereof, wherein the formulation has a pH of about 6.0. In another embodiment, the aqueous formulation of the present invention comprises a compound of Formula (I) as the acetate salt, complexed with a $^{67}$Cu ion, about 10% (v/v) ethanol, about 0.9% (w/v) sodium chloride, about 0.056% gentisic acid, or a salt thereof, and about 2.5 mg/mL L-methionine, or a salt thereof, wherein the formulation has a pH of about 6.0. In another embodiment, the aqueous formulation of the present invention comprises a compound of Formula (I) as the acetate, salt, complexed with a $^{67}$Cu ion, about 10% ethanol, about 0.9% (w/v) sodium chloride, not more than 0.056% gentisic acid, or a salt thereof, and about 2.5 mg/mL L-methionine, or a salt thereof, wherein the formulation has a pH of about 6.0.

In another embodiment, the formulations of the present invention may further comprise ascorbic acid, or a salt thereof, as an additional stabilizer.

The present inventors have found that the formulations provided according to the present invention have an increased radiochemical purity. The increased radiochemical purity of a formulation comprising a compound of Formula (I) and a Cu radioisotope is attributed to the use of one or more stabilizers in the formulation.

According to the present invention, a formulation of a complex of $^{64}$Cu and a compound of Formula (I) may have a radiochemical purity of at least about 90% for a time of at least 45 hours. This means that at least about 90% of the $^{64}$Cu radioisotope present in the formulation is complexed with the compound of Formula (I), or a salt thereof, for at least 45 hours after preparation of the formulation. Where the $^{64}$Cu radioisotope present in the formulation is not complexed with the compound of Formula (I), or a salt thereof, the $^{64}$Cu radioisotope may be present as a free $^{64}$Cu ion, or as part of a radiolysis product.

In an embodiment, the radiochemical purity of a formulation of the present invention comprising a complex of $^{67}$Cu and a compound of Formula (I), or a salt thereof is about 90% at a time of about 11 hours after preparation of the formulation. In another embodiment, the radiochemical purity of a formulation of the present invention comprising a complex of $^{67}$Cu and a compound of Formula (I), or a salt thereof is about 91% at a time of about 11 hours after preparation of the formulation. In another embodiment, the radiochemical purity of a formulation of the present invention comprising a complex of $^{67}$Cu and a compound of Formula (I), or a salt thereof is about 92% at a time of about 11 hours after preparation of the formulation. In another embodiment, the radiochemical purity of a formulation of the present invention comprising a complex of $^{67}$Cu and a compound of Formula (I), or a salt thereof is about 93% at a time of about 11 hours after preparation of the formulation. In another embodiment, the radiochemical purity of a formulation of the present invention comprising a complex of $^{67}$Cu and a compound of Formula (I), or a salt thereof is about 94% at a time of about 11 hours after preparation of the formulation. In another embodiment, the radiochemical purity of a formulation of the present invention comprising a complex of $^{67}$Cu and a compound of Formula (I), or a salt thereof is about 95% at a time of about 11 hours after preparation of the formulation. In another embodiment, the radiochemical purity of a formulation of the present invention comprising a complex of $^{67}$Cu and a compound of Formula (I), or a salt thereof is about 96% at a time of about 11 hours after preparation of the formulation. In another embodiment, the radiochemical purity of a formulation of the present invention comprising a complex of $^{67}$Cu and a compound of Formula (I), or a salt thereof is about 97% at a time of about 11 hours after preparation of the formulation. In another embodiment, the radiochemical purity of a formulation of the present invention comprising a complex of $^{67}$Cu and a compound of Formula (I), or a salt thereof is about 98% at a time of about 11 hours after preparation of the formulation. In another embodiment, the radiochemical purity of a formulation of the present invention comprising a complex of $^{67}$Cu and a compound of Formula (I), or a salt thereof is about 99% at a time of about 11 hours after preparation of the formulation.

In an embodiment, the radiochemical purity of a formulation of the present invention comprising a complex of $^{67}$Cu and a compound of Formula (I), or a salt thereof is about 99% immediately after preparation of the formulation. In another embodiment, the radiochemical purity of a formulation of the present invention comprising a complex of $^{67}$Cu and a compound of Formula (I), or a salt thereof is about 99% after about 1 h after preparation of the formulation. In another embodiment, the radiochemical purity of a formulation of the present invention comprising a complex of $^{67}$Cu and a compound of Formula (I), or a salt thereof is about 99% after about 3 h after preparation of the formulation. In another embodiment, the radiochemical purity of a formulation of the present invention comprising a complex of $^{67}$Cu and a compound of Formula (I), or a salt thereof is about 99% after about 6 h after preparation of the formulation. In another embodiment, the radiochemical purity of a formulation of the present invention comprising a complex of $^{67}$Cu and a compound of Formula (I), or a salt thereof is about 99% after about 9 h after preparation of the formulation. In another embodiment, the radiochemical purity of a formulation of the present invention comprising a complex of $^{67}$Cu and a compound of Formula (I), or a salt thereof is about 99% after about 12 h after preparation of the formulation. In another embodiment, the radiochemical purity of a formulation of the present invention comprising a complex of $^{67}$Cu and a compound of Formula (I), or a salt thereof is about 99% after about 15 h after preparation of the formulation. In another embodiment, the radiochemical purity of a formulation of the present invention comprising a complex of $^{67}$Cu and a compound of Formula (I), or a salt thereof is about 99% after about 18 h after preparation of the formulation. In another embodiment, the radiochemical purity of a formulation of the present invention comprising a complex of $^{67}$Cu and a compound of Formula (I), or a salt thereof is about 99% after about 21 h after preparation of the formulation. In another embodiment, the radiochemical purity of a formulation of the present invention comprising a complex of $^{67}$Cu and a compound of Formula (I), or a salt thereof is about 99% after about 24 h after preparation of the formulation.

The present invention also relates to kits of a macrocyclic ligand. The kit comprises a container comprising a compound of Formula (II), or a salt thereof, and a container comprising a solution of a Cu ion. The present inventors have found that the kits disclosed herein allow for the preparation of formulations of a ligand-radioisotope complex, for example, a Cu radioisotope, where the dissociation of the radioisotope from the ligand and radiolysis owing to the radioisotope is minimised. The kit in turn provides a formulation of a ligand—radioisotope complex where the effective time for imaging or treatment using the complex is maximized. The kits of the present invention also allow for the preparation of the formulation just prior to administration to the patient. Such on-site preparation increases the time for which the formulation may be effective in vivo, which in turn provides improved efficacy of the radiolabeled complex for both therapeutic and diagnostic purposes.

According to another aspect of the present invention, there is provided a kit comprising a compound of Formula (II), or a pharmaceutically acceptable salt thereof, complexed with a Cu ion:

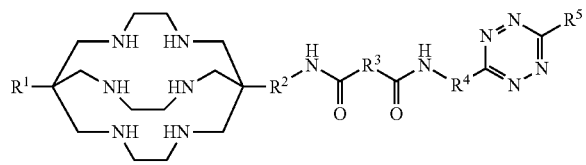

the kit comprising:
a container comprising a compound of Formula (I), or a pharmaceutically acceptable salt thereof;
a container comprising a solution of a Cu ion; and
instructions for preparing an aqueous formulation of a compound of Formula (I), or a salt thereof, complexed with a Cu ion, including the addition of a solution of ethanol and one or more stabilisers,
wherein:
$R^1$ is H, optionally substituted alkyl or optionally substituted amino;
$R^2$, $R^3$ and $R^4$ are linker groups; and
$R^5$ is H, optionally substituted alkyl, optionally substituted aryl or optionally substituted heteroaryl.

Like the compound of Formula (I), the compound of Formula (II) is also a macrocyclic sarcophagine ligand (3,6,10,13,16,19-hexaazabicyclo[6.6.6]eicosane, "sar") and contains a 1,2,4,5-tetrazine moiety at a terminal position of the compound. The tetrazine moiety in both compounds of Formula (I) and (II) consists of a six-membered ring, of which the four atoms at the 1, 2, 4 and 5 positions of the ring are nitrogen. This particular arrangement of the nitrogen atoms around the six-membered ring leads to an "s-tetrazine", which can participate in a click-type reaction with olefins. Specifically, the tetrazine functional group of the compounds of Formula (I) or (II) may undergo an inverse electron demand Diels-Alder cycloaddition with a transcyclooctene functional group, where the tetrazine acts as the dienophile and the transcyclooctene acts as the diene. The inverse electron demand Diels-Alder cycloaddition between the tetrazine of Formula (I) and a transcyclooctene occurs rapidly to provide the cyclized product. The rate at which the cycloaddition reaction proceeds between the tetrazine and the transcyclooctene may be affected by any substituents on each of these groups. The compounds of Formula (II) may have an additional substituent at the para position of the tetrazine ring. The tetrazine may also undergo a click-type reaction with other unsaturated compounds, which would lead to unwanted side products being produced. Given the presence of a number of heteroatoms in the tetrazine, the functional group and subsequently the compound itself may undergo decomposition.

As used herein, the term "alkyl" refers to a group or part of a group that contains a straight or branched aliphatic hydrocarbon group, preferably a $C_1$-$C_{12}$ alkyl, more preferably a $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

As used herein, the term "alkenyl" refers to a group or part of a group that is an aliphatic hydrocarbon group containing at least one carbon-carbon double bond and which may be straight or branched, preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

As used herein, the term "alkynyl" refers to a group or part of a group that is an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

As used herein, the term "aryl" refers to a group or part of a group that is (i) an optionally substituted monocyclic, or fused polycyclic, aromatic carbocycle (ring structure having ring atoms that are all carbon) preferably having from 5 to 12 atoms per ring, where examples of aryl groups include phenyl, naphthyl, and the like; (ii) an optionally substituted partially saturated bicyclic aromatic carbocyclic moiety in which a phenyl and a $C_5$-$C_7$ cycloalkyl or $C_5$-$C_7$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

As used herein, the term "cycloalkyl" refers to a saturated monocyclic or fused or spiro polycyclic, carbocycle, preferably containing from 3 to 9 carbons per ring, such as cyclopropyl, cyclobutyl, cyclopentyl, cyclohexyl and the like, unless otherwise specified. The term "cycloalkyl" includes monocyclic systems such as cyclopropyl and cyclohexyl, bicyclic systems such as decalin, and polycyclic systems such as adamantane. A cycloalkyl group typically is a $C_3$-$C_9$ cycloalkyl group. The group may be a terminal group or a bridging group.

As used herein, the term "halogen" represents chlorine, fluorine, bromine or iodine.

As used herein, the term "heteroalkyl" refers to a straight- or branched-chain alkyl group, preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted $C_1$-$C_{12}$ alkyl, optionally substituted $C_3$-$C_{12}$ cycloalkyl, optionally substituted $C_6$-$C_{18}$ aryl, and optionally substituted $C_1$-$C_{18}$ heteroaryl. Exemplary heteroalkyls include alkyl ethers, secondary and tertiary alkyl amines, amides, alkyl sulfides, and the like. Examples of heteroalkyl groups also include hydroxy$C_1$-$C_6$ alkyl, $C_1$-$C_6$ alkyloxy$C_1$-$C_6$ alkyl, amino$C_1$-$C_6$ alkyl, $C_1$-$C_6$ alkylamino$C_1$-$C_6$ alkyl, and di($C_1$-$C_6$ alkyl)amino$C_1$-$C_6$ alkyl. The group may be a terminal group or a bridging group.

As used herein, the term "heteroaryl" refers to a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl groups include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl, 1-, 2-, or 3-indolyl, and 2-, or 3-thienyl. A heteroaryl group is typically a $C_5$-$C_{18}$ heteroaryl group. The group may be a terminal group or a bridging group.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)Ra, —C(=O)ORa, —C(=O)NR$^a$R$^b$, —C(=NOH)R$^a$, —C(=NR$^a$)NR$^b$R$^c$, —NR$^a$R$^b$, —NR$^a$C(=O)R$^b$, —NR$^a$C(=O)OR$^b$, —NR$^a$C(=O)NR$^b$R$^c$, —NR$^a$C(=NR$^b$)NR$^c$R$^d$, —NR$^a$SO$_2$R$^b$, —SR$^a$, —SO$_2$NR$^a$R$^b$, —OR$^a$, —OC(=O)NR$^a$R$^b$, —OC(=O)R$^a$ and acyl, wherein R$^a$, R$^b$, R$^c$ and R$^d$ are each independently selected from the group consisting of H, $C_1$-$C_{12}$ alkyl, $C_1$-$C_{12}$ haloalkyl, $C_2$-$C_{12}$ alkenyl, $C_2$-$C_{12}$ alkynyl, $C_2$-$C_{10}$ heteroalkyl, $C_3$-$C_{12}$ cycloalkyl, $C_3$-$C_{12}$cycloalkenyl, $C_2$-$C_{12}$heterocycloalkyl, $C_2$-$C_{12}$ heterocycloalkenyl, $C_6$-$C_{18}$aryl, $C_1$-$C_{18}$heteroaryl, and acyl, or any two or more of $R^a$, $R^b$, $R^c$ and $R^d$, when taken together with the atoms to which they are attached form a heterocyclic ring system with 3 to 12 ring atoms.

In some embodiments, each optional substituent is independently selected from the group consisting of: halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, $CH_3$, $CH_2CH_3$, OH, $OCH_3$, $CF_3$, $OCF_3$, $NO_2$, $NH_2$, and CN.

As used herein, the term "$C_1$-$C_{12}$ alkylene" refers to a bivalent straight or branched chain aliphatic hydrocarbon group, where the group has 1 to 12 carbon atoms in the chain.

As used herein, the term "arylene" refers to a bivalent aromatic hydrocarbon group.

In some embodiments, the linker $R^2$ in the compound of Formula (II) is absent. In some embodiments, $R^2$ comprises an arylene group. In some embodiments, $R^2$ further comprises an amino group. In some embodiments, $R^2$ comprises an arylene group and an amino group, separated by an alkylene group. In some embodiments, $R^2$ comprises one or more alkylene groups that link an amino group and an arylene group to the remainder of the compound of Formula (I). In some embodiments, $R^2$ is an aminobenzylene group.

In some embodiments, the linker $R^3$ in the compound of Formula (II) is an optionally substituted $C_1$-$C_{12}$ alkylene group. In an embodiment, $R^3$ is an optionally substituted $C_3$ alkylene group. In an embodiment, $R^3$ is an unsubstituted $C_3$ alkylene group.

In some embodiments, the linker $R^4$ in the compound of Formula (II) is an optionally substituted arylene group. In some embodiments, $R^4$ is an optionally substituted benzylene group.

The compound of Formula (II) may further comprise a substituting group at the 4-position or para position of the tetrazine ring, i.e. $R^5$ in the compound of Formula (II). In some embodiments, $R^5$ is H. In some embodiments, $R^5$ is an optionally substituted alkyl group. In some embodiments, $R^5$ is an optionally substituted aryl group. In some embodiments, $R^5$ is an optionally substituted heteroaryl group. In some embodiments, $R^5$ is a haloalkyl group.

In an embodiment, the compound of Formula (II) is:

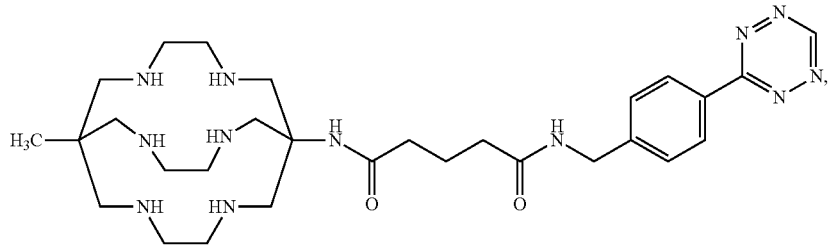

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) or (II) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic and arylsulfonic. Additional information on pharmaceutically acceptable salts can be found in *Remington's Pharmaceutical Sciences*, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

The compound of Formula (II) may comprise substitutions at the terminal position of the cage, i.e. $R^1$ in the compound of Formula (II). In some embodiments, $R^1$ may be an optionally substituted $C_1$-$C_{12}$ alkyl group. In other embodiments, $R^1$ may be an optionally substituted amino group.

The compound of Formula (II) comprises various linker groups denoted as $R^2$, $R^3$ and $R^4$.

which is a methyl-substituted sarcophagine with a series of linkers between the sarcophagine and the tetrazine. This compound is also known as N1-(4-(1,2,4,5-tetrazin-3-yl)benzyl)-N5-(8-methyl-3,6,10,13,16,19-hexaazabicyclo [6.6.6]icosan-1-yl)glutaramide and is abbreviated as MeCOSar-Tz.

The compound of Formula (II) in the kits of the present invention may be provided as a solid. In some embodiments, the compound of Formula (I) may be provided in a container as a lyophilized solid. In some embodiments, a kit of the present invention may comprise the compound of Formula (II) in a container as a lyophilized solid. In some embodiments, a kit of the present invention may comprise the compound of Formula (II) as a lyophilized solid in a container with additional additives in the same container.

The kits of the present invention comprise a container of a copper (Cu) ion. In an embodiment, the kit of the present invention comprises a container providing a solution of a Cu ion. In some embodiments, the Cu ion is provided as a Cu salt. In some embodiments, the Cu salt is a $Cu^I$ salt. In other embodiments, the Cu salt is a $Cu^{II}$ salt. In further embodiments, the Cu salt is a $Cu^{III}$ salt. In an embodiment, the kit of the present invention comprises a container providing a solution of a Cu radionuclide. In an embodiment, the kit of the present invention comprises a container with a solution of a Cu radioisotope. In an embodiment, the Cu radioisotope may be $^{60}$Cu. In another embodiment, the Cu radioisotope may be $^{61}$Cu. In another embodiment, the Cu radioisotope may be $^{64}$Cu. In another embodiment, the Cu radioisotope may be $^{64}$Cu. In some embodiments, the Cu radioisotope is provided in a solution of hydrochloric acid. The concentration of the hydrochloric acid solution in which the Cu radioisotope is provided may be from 0.01 M to 0.1 M. In some embodiments, the concentration of the hydrochloric acid solution in which the Cu radioisotope is provided is about 0.05 M.

The kits of the present invention also comprise instructions for preparing an aqueous formulation of the compound of Formula (II) complexed with a Cu ion, from the container comprising a compound of Formula (II) and the container comprising a solution of a Cu ion. The Cu ion in the kits of the present invention may be provided as a solution. In some embodiments, the Cu ion is provided in a container as a solution of the corresponding chloride salt of the Cu ion. In some embodiments, the Cu ion is provided in a container as a hydrochloric acid solution of the corresponding chloride salt of the Cu ion. In some embodiments, the Cu ion is a radioisotope and is provided in a container that shields radioactivity from the environment. In some embodiments, the Cu ion is a radioisotope provided in a container obtained from a synchrotron.

The kits of the present invention may further comprise a container consisting of a solution of ethanol and a stabilizer. Alternatively, the kit may provide instructions for the addition of a solution of ethanol and a stabilizer. The present inventors have found that the presence of one or more stabilizers assists in preventing or minimizing radiolysis of the complex of Formula (II) and Cu in the aqueous formulation obtained from the kits of the present invention. As for the formulations of compounds of Formula (I), examples of stabilizers that may be used in the present kits include thiosulfates, ascorbates, ascorbic acid, gentisates, gentisic acid, L-methionine, maltose, inositol, benzyl alcohol, trehalose, povidone, niacinamide, cysteine and where appropriate, salts thereof. In an embodiment, the kit comprises a container comprising of a solution of ethanol and a stabilizer. In another embodiment, the kit comprises a container comprising of a solution of ethanol and one or more stabilizers. In an embodiment, the stabilizer is gentisic acid, or a salt thereof. In another embodiment, the stabilizer is L-methionine, or a salt thereof.

The kits of the present invention may further comprise additional additives. Examples of additives include, but are not limited to, salts, such as sodium chloride, buffering agents, such as ammonium acetate and similar compounds. In some embodiments, the kits of the present invention comprise one or more additives that are provided in individual containers. In some embodiments, the kits of the present invention comprise one or more additives that are provided in containers intended for other components of the kit.

According to certain aspects of the present invention, the formulations and kits defined herein comprise ethanol. The ethanol used in the formulation may be anhydrous ethanol. Alternatively, the ethanol used in the formulation may not have been subject to drying processes and may be hydrated. The ethanol is preferably pharmaceutical grade ethanol. The ethanol present in the formulations of the present invention may further assist, when in combination with the one or more stabilizers in the formulation, in preventing radiolysis of the radiolabelled complex of Formula (I).

In an embodiment, ethanol is present in the formulation in an amount of about 7% to about 13% (v/v). In an embodiment, ethanol is present in the formulation in an amount of about 7% (v/v). In another embodiment, ethanol is present in the formulation in an amount of about 8% (v/v). In another embodiment, ethanol is present in the formulation in an amount of about 9% (v/v). In another embodiment, ethanol is present in the formulation in an amount of about 10% (v/v). In another embodiment, ethanol is present in the formulation in an amount of about 11% (v/v). In another embodiment, ethanol is present in the formulation in an amount of about 12% (v/v). In another embodiment, ethanol is present in the formulation in an amount of about 13% (v/v). In a preferred embodiment, ethanol is present in the formulation in an amount of about 10% (v/v). In other embodiments, the present invention also contemplates ethanol in ranges between the aforementioned amounts.

The kits of the present invention also comprise ethanol. In some embodiments, the ethanol may be provided in a container of the kit. In some embodiments, the ethanol may be provided in a container with the stabilizer of the kit. In some embodiments, the ethanol may be provided in a container with the one or more additional additives of the kit. In some embodiments, the ethanol may be provided in a container with the stabilizer and the one or more additives of the kit. In some embodiments, the ethanol is not provided with the kit and is instead provided by the end user of the kit.

The kits of the present invention may comprise an additional container with further additives. Examples of such additives include organic and inorganic salts, or solutions thereof. The container comprising a further additive of the kit may provide the further additive as a solid or as part of a solution. In an embodiment, the kits of the present invention further comprise sodium chloride or a solution thereof. In an embodiment, the kits of the present invention further comprise ammonium acetate or a solution thereof.

In an embodiment, a kit of the present invention comprises a container comprising a compound of Formula (II) or a salt thereof, a container comprising a solution of a Cu ion and instructions for preparing an aqueous formulation of a compound of Formula (II), or a salt thereof, complexed with a Cu ion. In an embodiment, a kit of the present invention comprises a container comprising a compound of Formula (II) or a salt thereof, a container comprising a solution of a Cu ion, a container comprising a solution of ethanol and one or more stabilizers and instructions for preparing an aqueous formulation of a compound of Formula (II), or a salt thereof, complexed with a Cu ion.

In an embodiment, a kit of the present invention comprises the compound:

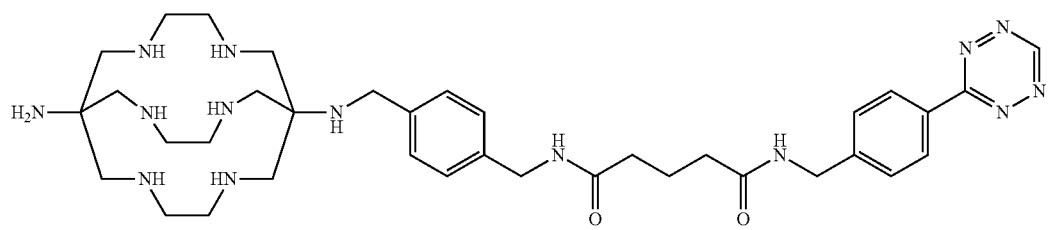

or a salt thereof, a container comprising a solution of a Cu ion and instructions for preparing an aqueous formulation of the compound, or a salt thereof, complexed with a Cu ion.

In an embodiment, a kit of the present invention comprises the compound:

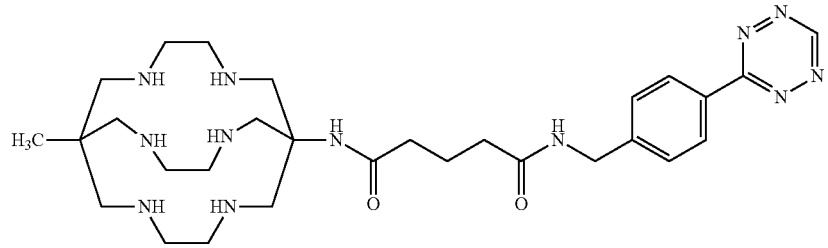

or a salt thereof, a container comprising a solution of a Cu ion and instructions for preparing an aqueous formulation of the compound, or a salt thereof, complexed with a Cu ion.

In an embodiment, a kit of the present invention comprises the compound:

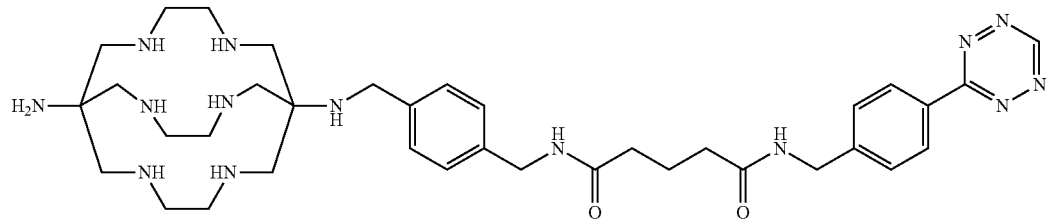

or a salt thereof, a container comprising a solution of a Cu radioisotope and instructions for preparing an aqueous formulation of the compound, or a salt thereof, complexed with a Cu radioisotope.

In an embodiment, a kit of the present invention comprises the compound:

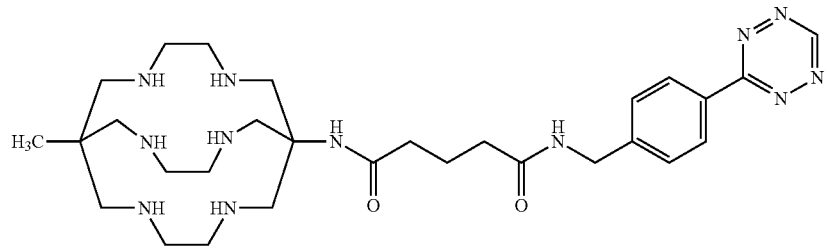

or a salt thereof, a container comprising a solution of a $^{64}$Cu radioisotope and instructions for preparing an aqueous formulation of the compound, or a salt thereof, complexed with a $^{64}$Cu radioisotope.

In an embodiment, a kit of the present invention comprises the compound:

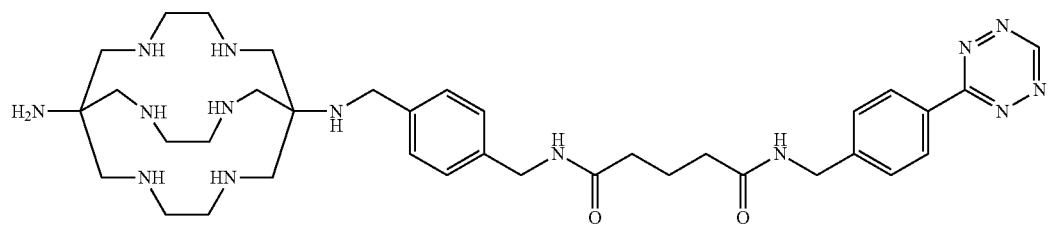

or a salt thereof, a container comprising a solution of a $^{64}$Cu radioisotope, a container comprising a solution of ethanol and a stabilizer and instructions for preparing an aqueous formulation of the compound, or a salt thereof, complexed with a $^{64}$Cu radioisotope.

In an embodiment, a kit of the present invention comprises the compound:

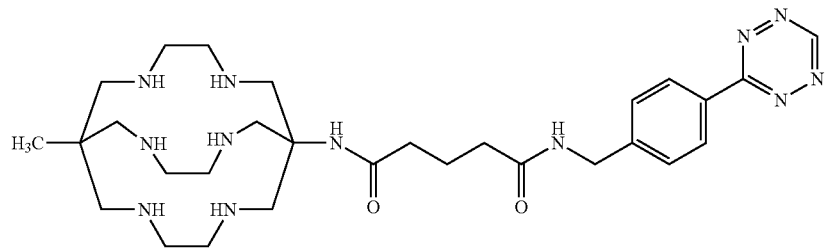

or a salt thereof, a container comprising a solution of a $^{64}$Cu radioisotope, a container comprising a solution of ethanol and one or more stabilizers and instructions for preparing an aqueous formulation the compound, or a salt thereof, complexed with a $^{64}$Cu radioisotope.

In an embodiment, a kit of the present invention comprises the compound:

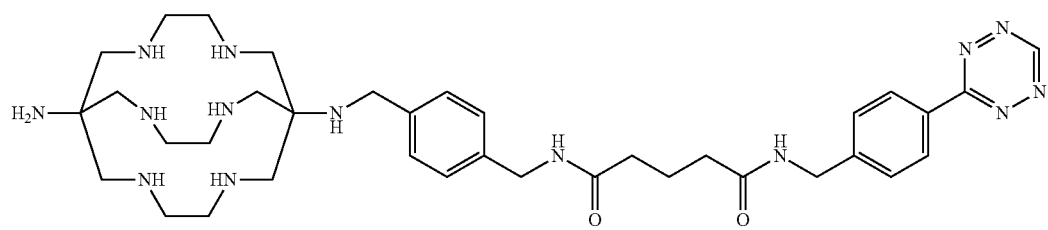

or a salt thereof, a container comprising a solution of a $^{67}$Cu radioisotope, a container comprising a solution of ethanol and one or more stabilizers and instructions for preparing an aqueous formulation of the compound, or a salt thereof, complexed with a $^{67}$Cu radioisotope.

In an embodiment, a kit of the present invention comprises the compound:

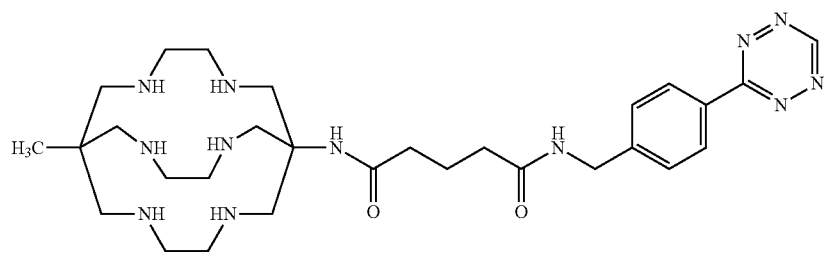

or a salt thereof, a container comprising a solution of a $^{67}$Cu radioisotope, a container comprising a solution of ethanol and one or more stabilizers and instructions for preparing an aqueous formulation of the compound, or a salt thereof, complexed with a $^{67}$Cu radioisotope.

Uses of a Formulation of the Present Invention

Formulations of the present invention and formulations derived from kits of the present invention may be particularly useful for the purposes of diagnosis and treatment in medicine. Complexes with a ligand bearing an appropriate targeting fragment can be used to locate specific tissue types. For such complexes to be considered suitable for use in in vivo diagnosis and treatment, the complex must display appropriate kinetic, stability and clearance properties under physiological conditions, in addition to the requisite solubility and stability properties of the complex in solution. As used herein, the term "complex" may relate to a ligand-metal ion complex, where the metal ion is a radioactive isotope or alternatively, the metal ion is a non-radioactive isotope.

Accordingly, the present invention provides a method for radioimaging, a method for diagnosing a disease in a subject or a method for therapy of a disease in a subject, comprising administering to the subject an effective amount of a formulation as defined herein. The present inventors have found that the formulations of the present invention may be used in a method for radioimaging, a method for diagnosing or a method for therapy of a cancer.

As used herein the term "cancer" broadly encompasses a class of neoplastic diseases characterised with abnormal cell growth with the potential to invade or spread to other parts of the body. These are to be contrasted with benign tumours, which do not spread to other parts of the body and therefore the definition as used herein includes all malignant (cancerous) disease states. The term therefore encompasses the treatment of tumours.

Accordingly, the term "tumour" is used generally to define any malignant cancerous or pre-cancerous cell growth, and may include leukemias, but is particularly directed to solid tumours or carcinomas such as melanomas, colon, lung, ovarian, skin, breast, pancreas, pharynx, brain, prostate, CNS, and renal cancers (as well as other cancers).

As described herein, the formulations and the kits of the present invention comprise a compound of Formula (I) or (II), which each contain a tetrazine functionality. The tetrazine group can participate in an inverse electron demand Diels-Alder (IEDDA) reaction with a transcyclooctene functional group. The transcyclooctene is installed on an antibody that specifically targets tumour cells and/or surfaces. For example, the huA33 antibody is a monoclonal antibody that recognises the A33 antigen and targets colorectal cancer. The huA33 antibody is first modified to produce a transcyclooctene-huA33 antibody conjugate, which is then administered to a subject. As the antibody targets the A33 antigen, localisation of the antibody conjugate on the surfaces of colorectal cancer tumours occurs due to the expression of the antigen by the tumour. With the surface of the tumour now bearing a free transcyclooctene group, a formulation of the present invention is then administered to the subject. The tetrazine group of the compound of Formula (I) or (II) selectively reacts with the transcyclooctene group on the modified antigen-antibody complex on the surface of the tumour, with the IEDDA reaction occurring to produce the corresponding cycloaddition product. The present inventors have found that a complex of the compound of Formula (I) or (II) and a Cu ion, as found in the formulations of the present invention, has shown particular utility in binding to an antibody expressing a transcyclooctene group installed in a pretargeting strategy. In certain embodiments, the formulations of the present invention may be used in the radioimaging, diagnosis or the treatment of a cancer, where the transcyclooctene group is expressed or highly expressed, as a result of the expression of an antigen to which the transcyclooctene-bound antibody targets. In an embodiment, the formulations of the present invention comprising a compound of Formula (I) or (II) are administered to a subject after the pretargeting step (i.e. the introduction of the transcyclooctene moiety). The formulations of the present invention provide stability to the complex of a compound of Formula (I) or (II) and a radioisotope prior to administration.

The present inventors have found that using a pretargeting strategy for the imaging of colorectal cancer using a Cu radioisotope allows for images of greater contrast to be obtained, since the tumour site specifically has a transcyclooctene group and is thus clearly delineated from the surrounding tissues. This reduces the background radiation, or radioactivity due to binding of the radioisotope complex at other sites, which in turn allows for images of better contrast and higher quality to be obtained. The present inventors have found that the combination of excipients and a compound of Formula (I) or (II) allow for the delivery of the compound of Formula (I) or (II) or a complex with a Cu radioisotope thereof to the desired site of action, owing to the stability of the compound or complex as provided by the excipients. In an embodiment, the formulations of the present invention administered to a subject are allowed to clear from the system of the subject prior to imaging of the radioisotope complexed to the compound of Formula (I) or (II). The present inventors have also found that the formulations of the present invention allow for adequate clearance of the compound of Formula (I) or (II), or complexes thereof, from the system of the subject to which the formulation is administered. The clearance of the radioisotope-bound complex from the subject allows for images of a higher contrast to be obtained, as the background radiation in the subject owing to any free radioisotope-Formula (I) complex being eliminated from the system.

The aqueous formulations and formulations provided by a kit of the present invention comprise a compound of Formula (I) or (II) containing a tetrazine motif, which binds selectively to the transcyclooctene functionality of a modified huA33 antigen. A person skilled in the art would understand that modifying a different antibody to contain a transcyclooctene functionality would also allow for the selective binding of the compound of Formula (I) or (II) to a different antigen. Since a different antigen would bind to a different site in vivo, the compound of Formula (I) or (II) complexed with a radioisotope would deliver the radioisotope and the associated radioactivity to a different site of action. Subsequently, the present invention provides for the binding of a compound of Formula (I) or (II), or a complex thereof, to an antibody or other moiety that comprises a transcyclooctene functional group.

The radioisotope-ligand complex of the present invention may comprise a radioisotope such as $^{64}$Cu. The $^{64}$Cu isotope has a half-life of approximately 12.7 hours and decays by both positron emission and beta decay, which makes the use of a $^{64}$Cu-labelled complex suitable for use in various modes of radioimaging. In particular, the decay characteristics and half-life of $^{64}$Cu make this radioisotope a favourable choice for use in positron emission tomography (PET) and single-photon emission computed tomography (SPECT). The radioisotope-ligand complex of the present invention may comprise a radioisotope such as $^{61}$Cu. The $^{61}$Cu isotope has a half-life of approximately 3 hours and decays by positron emission, which makes the use of a $^{61}$Cu-labelled complex suitable for use in various modes of radioimaging. The radioisotope-ligand complex of the present invention may also comprise a radioisotope such as $^{67}$Cu. The $^{67}$Cu isotope has a half-life of approximately 61.8 hours and decays by beta emission, which makes the use of a $^{67}$Cu-labelled complex suitable for use in SPECT imaging. The $^{67}$Cu-labelled complex may also be suitable for use as a radiotherapy treatment.

The administration of an effective amount of a formulation or a formulation provided by a kit of the present invention comprising a compound of Formula (I) or (II) and a Cu radioisotope, such as $^{60}$Cu, $^{61}$Cu, $^{64}$Cu or $^{67}$Cu, may lead to the binding of the complex of the compound of Formula (I) or (II) and the Cu radioisotope to somatostatin receptors. Where the somatostatin receptors are expressed on the surface of a tumour, the complex of a compound of Formula (I) or (II) and a Cu ion may bind to the somatostatin receptors. In an embodiment, the present invention provides a method for radioimaging, comprising administering to the subject a formulation comprising a compound of Formula (I) or (II) and a Cu ion. In an embodiment, a formulation comprising a compound of Formula (I) or (II) and a $^{64}$Cu or $^{67}$Cu ion may be used in a method for radioimaging. Monitoring of a subject to which a formulation comprising a compound of Formula (I) or (II) and a Cu radioisotope was administered by PET or SPECT, for example, allows for the visualisation and subsequent detection of tumour sites. The visualisation information obtained by radioimaging may provide information in relation to the location of any such tumour sites. Monitoring of the subject to which the radiolabelled complex was administered by SPECT, for example, allows for the visualisation and subsequent detection of tumour sites. This provides information in relation to the location of the tumours, where present. Repeated imaging at later time points allows for monitoring clearance of the radioisotope-ligand complex, which enables dosimetry estimates to be calculated. A person skilled in the art would understand that the amount to be administered in order to facilitate radioimaging may vary and will subsequently depend on the nature of the subject and the intended site of imaging.

In order for the complex to be suitable for radioimaging purposes, the radioisotope-ligand complex must display sufficient metabolic stability, i.e. that the complex remains intact with the radioisotope bound to the ligand, for a requisite time. The formulations or formulations provided by a kit of the present invention provide a complex of a compound of Formula (I) or (II) and a $^{64}$Cu radioisotope that may remain intact for up to 45 hours, which may be evidenced by the absence of radioisotope loss and metabolic decomposition. The formulations or formulations provided by a kit of the present invention also provide a complex of a compound of Formula (I) or (II) and a $^{67}$Cu radioisotope.

The formulations of the present invention or formulations provided by a kit of the present invention may be administered to a subject for the purposes of radioimaging, diagnosis or therapy. Administration is by a parenteral route, with administration by intravenous injection preferred. Alternatively, the formulations of the present invention may be given by intraarterial or other routes, for delivery into the systemic circulation. The subject to which the formulation is administered is then placed into a PET scanner and images showing the localisation of the radioisotope-ligand complex, and subsequently location of any tumours, are obtained. This then allows for diagnosis and detection of tumours. Alternatively, a sample (for example, a blood or a tissue sample) that has been exposed to a formulation of the present invention may be analysed by gamma spectroscopy, gamma counting, liquid scintillation counting, autoradiography or beta probe in order to obtain radioimages.

In an embodiment, the present invention provides the use of a formulation or a formulation provided by a kit of the present invention comprising a compound of Formula (I) or (II) and a radioisotope, in a method for the radioimaging of a tumour or cancer. One skilled in the art would understand that the information obtained from radioimaging of a subject may be used in the diagnosis of a tumour or cancer in the subject. In an embodiment, the present invention provides a method for the diagnosis of a tumour or cancer in a subject.

Where the formulation of the present invention or formulation provided by a kit derived of the present invention comprises a compound of Formula (I) or (II) and a Cu radioisotope, the administration of the formulation may treat a tumour or cancer. As discussed above, the compound of Formula (I) or (II) may bind to antibodies on the surface of a tumour or cancer site, which are themselves bound to an antigen on the surface of the tumour or cancer site. This brings the Cu radioisotope into close proximity of this location. As the Cu radioisotope undergoes radioactive decay, with the mode of decay dependent on the exact radioisotope chosen, the products of decay may be useful in the treatment of a tumour or cancer due to the proximity of the tumour or cancer to the compound of Formula (I) or (II) and Cu radioisotope. In an embodiment, the present invention provides the use of a formulation or a formulation derived from a kit of the present invention comprising a compound of Formula (I) or (II) and a Cu radioisotope in a method for the treatment of a tumour or cancer in a subject.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

EXAMPLES

Example 1

Preparation of a Low-Dose $^{64}$Cu-SarAr-Tz Formulation, Incorporating Ethanol and Sodium Gentisate as Excipients to Reduce Radiolysis A buffer solution of 0.1 M ammonium acetate may be prepared, where the buffer solution also contains ethanol at a concentration of 4-10% (v/v). The buffer solution may contain sodium gentisate, where a 5 mL volume of the buffer solution contains 38 mg of sodium gentisate.

The SarAr-Tz compound may be obtained as a lyophilised powder. 20 μg of SarAr-Tz in its lyophilised form may be dissolved in 5 mL of the prepared buffer solution.

A solution of [$^{64}$Cu]CuCl$_2$ in 0.05 M hydrochloric acid may be prepared, where a 300 μL volume of this solution contains 1500 MBq of [$^{64}$Cu]. A 300 μL volume of this [$^{64}$Cu]CuCl$_2$ solution may be added to the solution containing SarAr-Tz and sodium gentisate in ammonium acetate buffer. This combined solution may be allowed to stand, without stirring, at room temperature for 15 minutes.

The solution may then be filtered through a solid phase extraction cartridge. The cartridge may be eluted with 1.0 mL ethanol and then 9.0 mL saline solution into a sterile product vial, to give $^{64}$Cu-SarAr-Tz in a volume of 10 mL ethanol/saline solution. HPLC analysis of the solution obtained may be used to determine the radiochemical purity of the formulation. Further HPLC analysis of the same product solution obtained over multiple time points may be used to show that the radiochemical purity remains at a certain level for a time.

Example 2

Preparation of a High-Dose $^{64}$Cu-SarAr-Tz Formulation, Incorporating Ethanol, Sodium Gentisate and L-Methionine as Excipients to Reduce Radiolysis A buffer solution of 0.1 M ammonium acetate may be prepared, where the buffer solution also contains ethanol at a concentration of 4-10% (v/v). The buffer solution may also contain sodium gentisate, where a 5 mL volume of the buffer solution contains 114 mg of sodium gentisate.

The SarAr-Tz compound may be obtained as a lyophilised powder. 20 μg of SarAr-Tz in its lyophilised form may be dissolved in 5 mL of the prepared buffer solution.

A solution of [$^{64}$Cu]CuCl$_2$ in 0.05 M hydrochloric acid may be prepared, where a 300 µL volume of this solution contains 4650 MBq of [$^{64}$Cu]. A 300 µL volume of this [$^{64}$Cu]CuCl$_2$ solution may be added to the solution containing SarAr-Tz and sodium gentisate in ammonium acetate buffer. This combined solution may be allowed to stand, without stirring, at room temperature for 15 minutes.

The solution may be filtered through a solid phase extraction cartridge. The cartridge may then be eluted with 1.0 mL ethanol and then 16.0 mL saline solution, to give $^{64}$Cu-SarAr-Tz in a volume of 20 mL ethanol/saline solution. HPLC analysis of the solution obtained may be used to determine the radiochemical purity of the formulation. Further HPLC analysis of the same product solution obtained over multiple time points may be used to show that the radiochemical purity remains at a certain level for a time.

Example 3

Preparation of a $^{67}$Cu-SarAr-Tz Formulation, Incorporating Ethanol, Sodium Gentisate and L-Methionine as Excipients to Reduce Radiolysis A buffer solution of 0.1 M ammonium acetate may be prepared, where the buffer solution also contains ethanol at a concentration of 4-10% (v/v). The buffer solution may also contain sodium gentisate, where a 5 mL volume of the buffer solution contains 114 mg of sodium gentisate.

The SarAr-Tz compound may be obtained as a lyophilised powder. 60 µg of SarAr-Tz in its lyophilised form may be dissolved in 5 mL of the prepared buffer solution.

A solution of [$^{67}$Cu]CuCl$_2$ in 0.05 M hydrochloric acid may be prepared, where a 300 µL volume of this solution contains 4650 MBq of [$^{64}$Cu]. A 300 µL volume of this [$^{67}$Cu]CuCl$_2$ solution may be added to the solution containing SarAr-Tz and sodium gentisate in ammonium acetate buffer. This combined solution may be allowed to stand, without stirring, at room temperature for 15 minutes.

The solution may be filtered through a solid phase extraction cartridge. The cartridge may then be eluted with 1.0 mL ethanol and then 16.0 mL saline solution into a sterile product vial containing a solution of L-methionine (50 mg in 3 mL saline solution), to give $^{67}$Cu-SarAr-Tz in a volume of 20 mL ethanol/saline solution. HPLC analysis of the solution obtained may be used to determine the radiochemical purity of the formulation. Further HPLC analysis of the same product solution obtained over multiple time points may be used to show that the radiochemical purity remains at a certain level for a time.

Example 4

Kit Comprising SarAr-Tz. and $^{64}$Cu

SarAr-Tz as a lyophilized solid is provided in one container of the kit. The Cu ion as a $^{64}$Cu radioisotope is provided in a different container as the chloride salt in a solution of hydrochloric acid at a concentration of 0.05 M HCl. A 300 µL volume of the $^{64}$Cu radioisotope solution contains about 4650 MBq of [$^{64}$Cu]. The instructions provided with the kit include details for the mixing of a buffer solution, addition of sodium chloride and ethanol, and mixing of SarAr-Tz and the solution of the Cu ion provided with the kit.

Example 5

Kit Comprising SarAr-Tz. and $^{64}$Cu

SarAr-Tz as a lyophilized solid is provided in one container of the kit. The Cu ion as a $^{64}$Cu radioisotope is provided in a different container as the chloride salt in a solution of hydrochloric acid at a concentration of 0.05 M HCl. A 300 µL volume of the $^{64}$Cu radioisotope solution contains about 4650 MBq of [$^{64}$Cu]. The kit also provides a container comprising sodium chloride and ethanol. The instructions provided with the kit include details for mixing of the lyophilized SarAr-Tz, Cu ion, sodium chloride and ethanol to provide an aqueous formulation of a Cu ion complex of a compound of SarAr-Tz.

Example 6

Kit Comprising SarAr-Tz.

SarAr-Tz as a lyophilized solid is provided in one container of the kit. The Cu ion as a $^{64}$Cu radioisotope is provided in a different container as the chloride salt in a solution of hydrochloric acid at a concentration of 0.05 M HCl. A 300 µL volume of the $^{64}$Cu radioisotope solution contains about 4650 MBq of [$^{64}$Cu]. The kit also provides a container comprising sodium chloride, gentisic acid and ethanol. The instructions provided with the kit include details for mixing of the lyophilized SarAr-Tz, Cu ion, sodium chloride, gentisic acid and ethanol.

Example 7

Kit Comprising MeCOSar-Tz.

MeCOSar-Tz as a lyophilized solid is provided in one container of the kit. The Cu ion as a $^{64}$Cu radioisotope is provided in a different container as the chloride salt in a solution of hydrochloric acid at a concentration of 0.05 M HCl. A 300 µL volume of the $^{64}$Cu radioisotope solution contains about 4650 MBq of [$^{64}$Cu]. The instructions provided with the kit include details for the mixing of a buffer solution, addition of sodium chloride and ethanol, and mixing of MeCOSar-Tz and the solution of the Cu ion provided with the kit.

The invention claimed is:
1. An aqueous formulation comprising a compound of Formula (I), or a salt thereof,

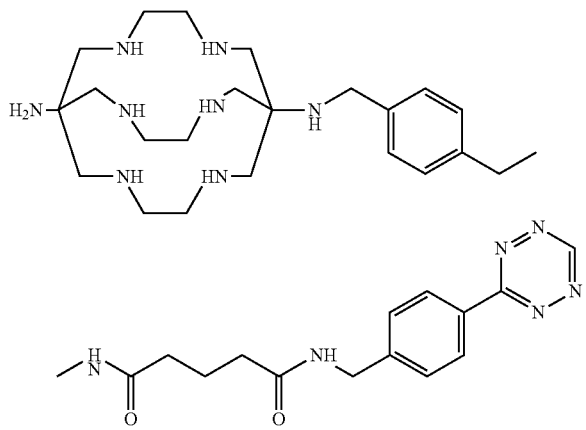

Formula (I)

the formulation further comprising:
about 0.6% to about 1.2% (w/v) sodium chloride;
about 0.06% (w/v) sodium gentisate;
about 1 mg/mL to about 4 mg/mL L-methionine, or a salt thereof; and
4% (v/v) to 10% (v/v) ethanol.
2. An aqueous formulation comprising a compound of Formula (I), or a salt thereof,

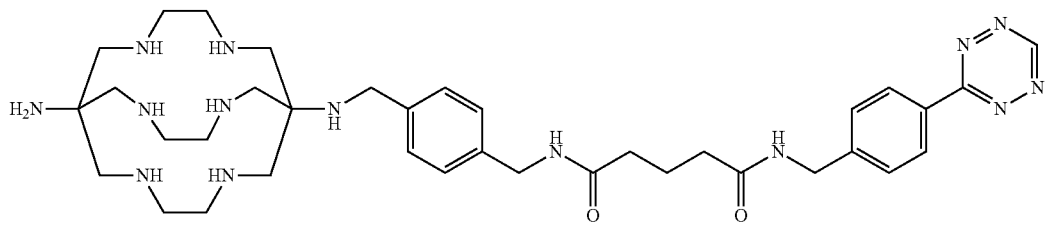

Formula (I)

the formulation further comprising:
about 0.6% (w/v) to about 1.2% (w/v) sodium chloride;
about 0.06% (w/v) sodium gentisate;
about 1 mg/mL to about 4 mg/mL L-methionine, or a salt thereof;
4% (v/v) to 10% (v/v) ethanol; and
an acetate salt.

3. An aqueous formulation according to claim 1, wherein the formulation has a pH of between about 4 to about 8.

4. An aqueous formulation according to claim 1, wherein the compound of Formula (I) is a hydrochloride salt.

5. An aqueous formulation according to claim 1, wherein the compound of Formula (I) is complexed with a Cu ion.

6. An aqueous formulation according to claim 5, wherein the Cu ion is a radioisotope.

7. An aqueous formulation according to claim 6, wherein the Cu radioisotope is selected from the group consisting of $^{60}$Cu, $^{61}$Cu, $^{64}$Cu and $^{67}$Cu.

8. A process for preparing an aqueous formulation comprising a compound of Formula (I), or a salt thereof, complexed with a Cu ion, the process comprising the steps of:
i) preparing a buffer solution of an acetate salt, wherein the buffering solution further comprises:
about 0.6% (w/v) to about 1.2% (w/v) sodium chloride;
about 0.06% (w/v) sodium gentisate; and
4% (v/v) to 10% (v/v) ethanol;
ii) dissolving a compound of Formula (I), or a salt thereof, in the buffering solution obtained from step i);
iii) adding a solution of a Cu ion to the solution obtained from step ii);
iv) filtering the solution obtained from step iii) on to a stationary phase; and
v) washing the stationary phase of step iv) with ethanol and saline into a solution of about 1 mg/mL to about 4 mg/mL L-methionine;
to recover an aqueous formulation comprising a compound of Formula (I), or a salt thereof, complexed with a Cu ion.

9. A process according to claim 8, wherein the Cu ion is a Cu radioisotope selected from the group consisting of $^{60}$Cu, $^{61}$Cu, $^{64}$Cu and $^{67}$Cu.

10. An aqueous formulation prepared by a process of claim 8.

11. An aqueous formulation of a compound of Formula (II), or a salt thereof, complexed with a Cu ion:

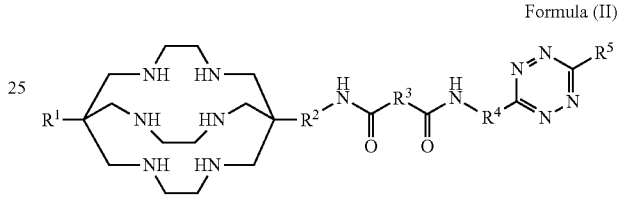

Formula (II)

wherein:
R$^1$ is H, optionally substituted alkyl or optionally substituted amino; and
R$^2$, R$^3$ and R$^4$ are linker groups; and
R$^5$ is H, optionally substituted alkyl, optionally substituted aryl or optionally substituted heteroaryl,
prepared according to a kit comprising:
a container comprising a compound of Formula (II), or a salt thereof;
a container comprising a solution of a Cu ion;
a container comprising 4% (v/v) to 10% (v/v) ethanol and about 0.06% (w/v) sodium gentisate; and
a container comprising 4% (v/v) to 10% (v/v) ethanol and about 0.6% to about 1.2% (w/v) sodium chloride; and
instructions for preparing an aqueous formulation of a compound of Formula (II), or a salt thereof, complexed with a Cu ion.

12. A method for radioimaging, diagnosing or treating a cancer, the method comprising administering to a subject in need thereof an aqueous formulation according to claim 1, the method further comprising monitoring the subject by PET or SPECT.

* * * * *